US009952691B2

(12) United States Patent
Heo et al.

(10) Patent No.: US 9,952,691 B2
(45) Date of Patent: Apr. 24, 2018

(54) TOUCH PANEL AND IMAGE DISPLAY DEVICE HAVING THE SAME

(71) Applicant: LG INNOTEK CO., LTD., Seoul (KR)

(72) Inventors: Seong Ho Heo, Seoul (KR); Myung Ki Min, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 430 days.

(21) Appl. No.: 14/697,748

(22) Filed: Apr. 28, 2015

(65) Prior Publication Data

US 2015/0324027 A1 Nov. 12, 2015

(30) Foreign Application Priority Data

May 9, 2014 (KR) .................. 10-2014-0055632
May 14, 2014 (KR) .................. 10-2014-0057823

(51) Int. Cl.
*G06F 3/041* (2006.01)

(52) U.S. Cl.
CPC .................... *G06F 3/041* (2013.01)

(58) Field of Classification Search
CPC ....................................... G06F 3/041
See application file for complete search history.

(56) References Cited

U.S. PATENT DOCUMENTS

| 2009/0315859 | A1 | 12/2009 | Chien et al. | |
| 2012/0212448 | A1* | 8/2012 | Lee | G06F 3/044 345/174 |
| 2012/0268418 | A1* | 10/2012 | Ishizaki | G06F 3/0412 345/174 |
| 2013/0240341 | A1* | 9/2013 | Lo | G06F 3/044 200/600 |
| 2014/0174902 | A1* | 6/2014 | Yang | G06F 3/044 200/600 |
| 2015/0015532 | A1* | 1/2015 | Choung | G06F 3/044 345/174 |

FOREIGN PATENT DOCUMENTS

KR 10-2014-0016709 A 2/2014

\* cited by examiner

*Primary Examiner* — Ariel Balaoing
(74) *Attorney, Agent, or Firm* — KED & Associates LLP

(57) ABSTRACT

A touch panel may include: a sensing electrode part including a plurality of first sensing electrodes and a plurality of second sensing electrodes insulated from the first sensing electrodes and crossing the first sensing electrodes; an opening part in the sensing electrode part; and a dummy pattern adjacent to the sensing electrode part.

20 Claims, 16 Drawing Sheets

FIG. 4
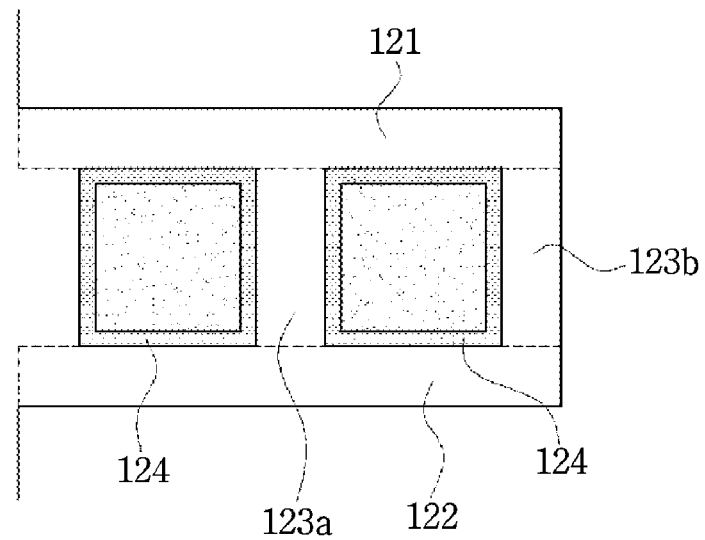
(a)
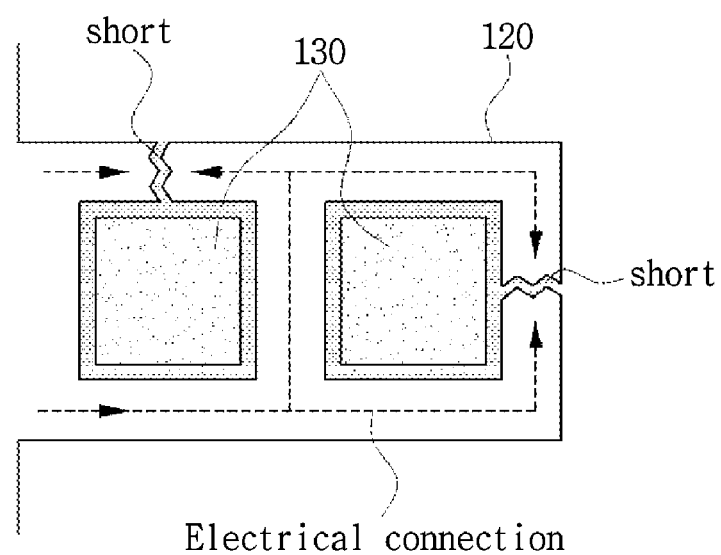
(b)

FIG. 9
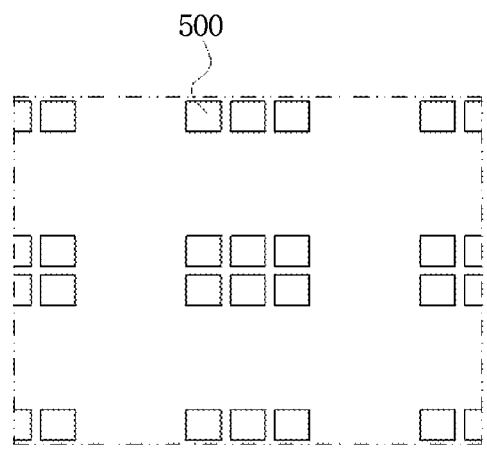
(a)
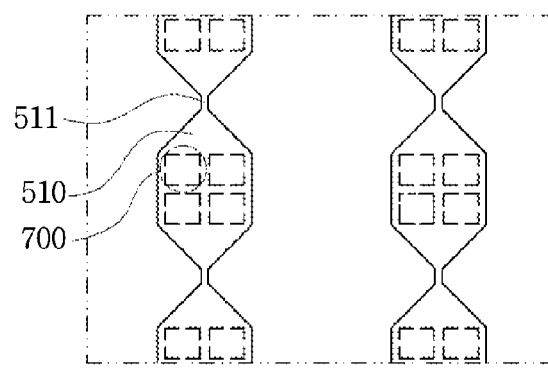
(b)
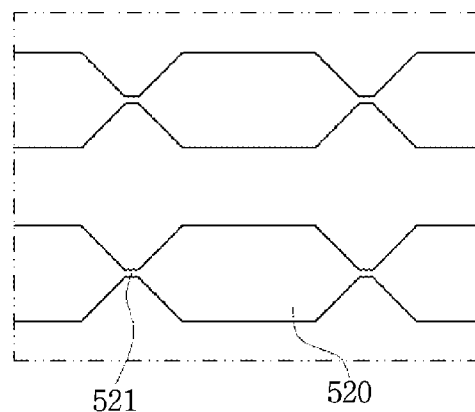
(c)

FIG. 12
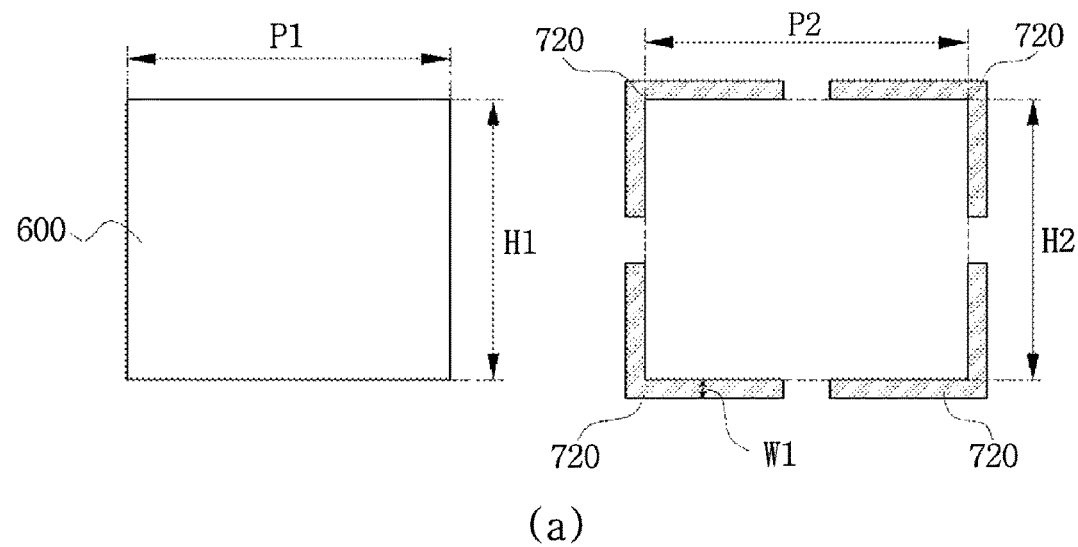
(a)
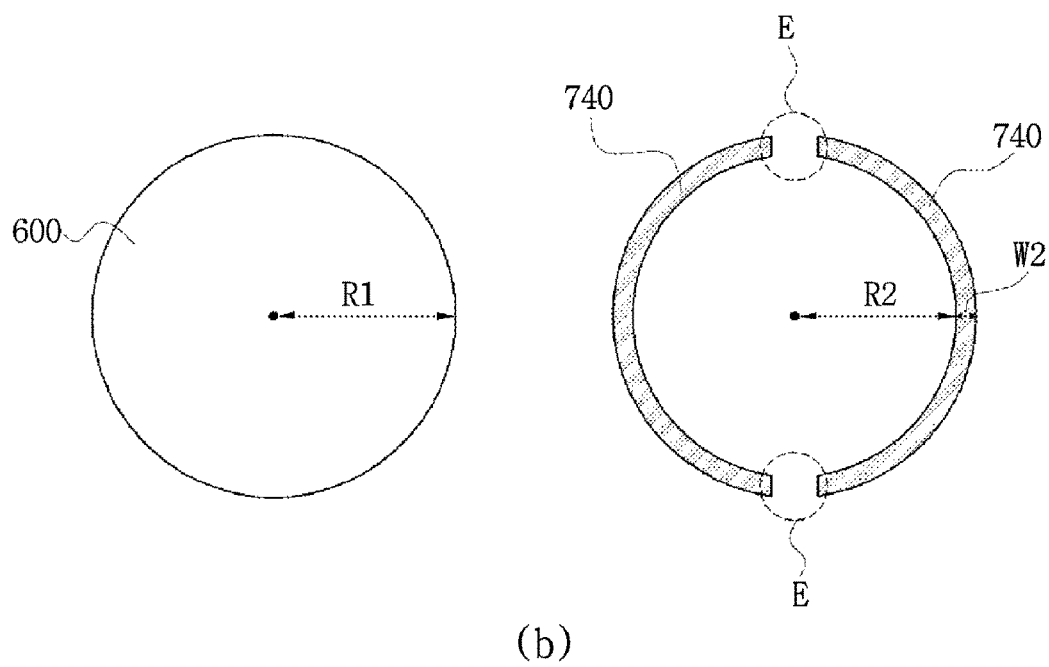
(b)

TOUCH PANEL AND IMAGE DISPLAY DEVICE HAVING THE SAME

CROSS-REFERENCE TO RELATED APPLICATIONS

This application claims under 35 U.S.C. § 119 to Korean Patent Application No. 10-2014-0055632 filed on May 9, 2014 and Korean Patent Application No. 10-2014-0057823 filed on May 14, 2014, whose entire disclosures are hereby incorporated by reference.

BACKGROUND

1. Field

The embodiment relates to a touch panel.

2. Background

A touch panel is a device capable of sensing information input by a touch scheme. A touch panel for sensing a touch input on an image display area by using a human hand or an object has been widely used in an electronic appliance such as personal digital assistants (PDA), a laptop computer, an office automation (OA) device, a medical device, or an automobile navigation system.

As a typical scheme of a touch panel for sensing a touch input from an outside, there have been known a capacitive scheme, a resistive scheme, an electromagnetic induction scheme, an optical scheme, etc., and recently, the capacitive scheme has been widely used.

Since the touch panel must be able to sense information input in a touch scheme as an electrical signal, the touch panel generally includes a sensing electrode for sensing touch stimulation and a circuit for receiving the variation of a signal generated from the sensing electrode. The sensing electrode has a structure in which sensing electrodes are disposed in both directions (for example, longitudinal and traversal directions) in order to sense the coordinates of touch stimulation applied thereto.

Due to the structural limitation of a sensing electrode for sensing a variation in electrostatic capacity, which is generated when a touch signal is applied, the visibility of the touch panel is deteriorated. Due to the difference in hue and light transmittance generated by discontinuity or irregularity of the sensing electrode formed on the touch panel, the sensing electrode is visually recognized or glitters, so that the visibility of the touch panel is increased.

To solve the above described problems, although a scheme of additionally forming a dummy pattern in a region between the sensing electrodes (that is, a region in which any sensing electrodes are not formed) may be considered, there is a limit to remove a phenomenon of increasing visibility due to the structure of the sensing electrode itself. There has been increased a need to provide a touch panel formed to have a shape capable of reducing the visibility.

Meanwhile, a part of a sensing electrode may be damaged due to an error occurring during various kinds of processes to be performed to form the sensing electrode on a substrate, so that the touch sensibility may be deteriorated at the damaged point. There has been increased a request of a technique capable of preventing the touch sensing performance from being deteriorated due to an error in a process of manufacturing a touch panel and a damage in real life.

BRIEF DESCRIPTION OF THE DRAWINGS

The embodiments will be described in detail with reference to the following drawings in which like reference numerals refer to like elements wherein:

FIG. 4 is a view illustrating the fact that, when several of the electrical connecting passages included in the sub-electrode depicted in FIG. 3 are damaged, the sub-electrode may be electrically connected to the main electrode through the remaining electrical connecting passages.

FIG. 9 shows plan views illustrating in more detail the arrangement of the sensing electrode part and dummy pattern depicted in FIG. 8.

FIG. 12 shows views illustrating the comparison of the dummy pattern and the first opening part in the touch panel according to the embodiment.

DETAILED DESCRIPTION

A touch panel according to the embodiment may include a view area V/A for displaying an image and a dead area D/A disposed at a periphery of the view area V/A to surround the view area V/A. A printing layer, which blocks light to allow a wire not to be viewed, may be formed on the dead area. For example, the printing layer may have a color such as black, white or blue. The color of the printing layer is not limited to the above, but the printing layer may have various colors if it can allow the wire not to be viewed.

Figure 1:
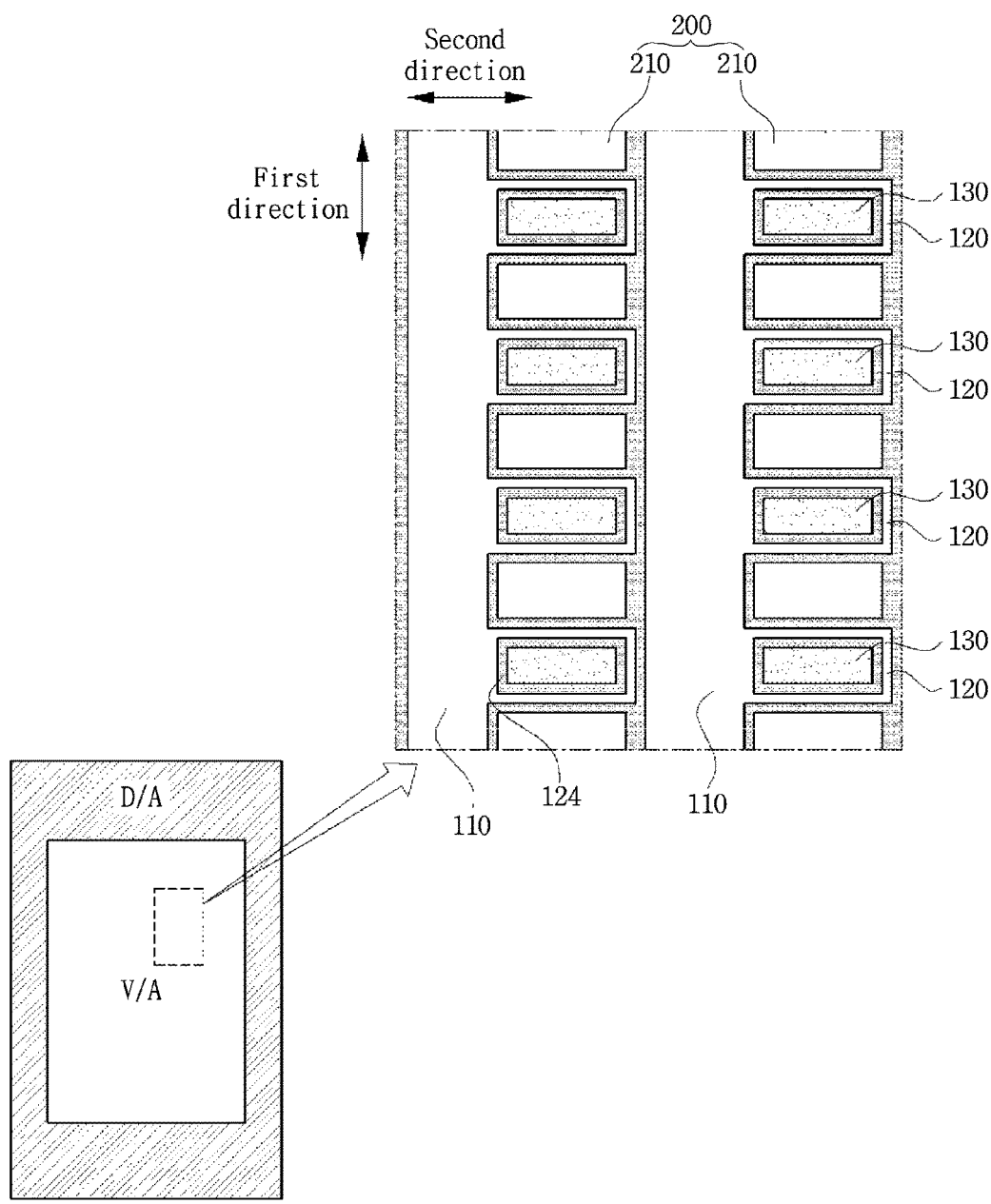
FIG. 1 is a schematic plan view showing a touch panel including an improved sensing electrode according to the first embodiment.
Figure 2:
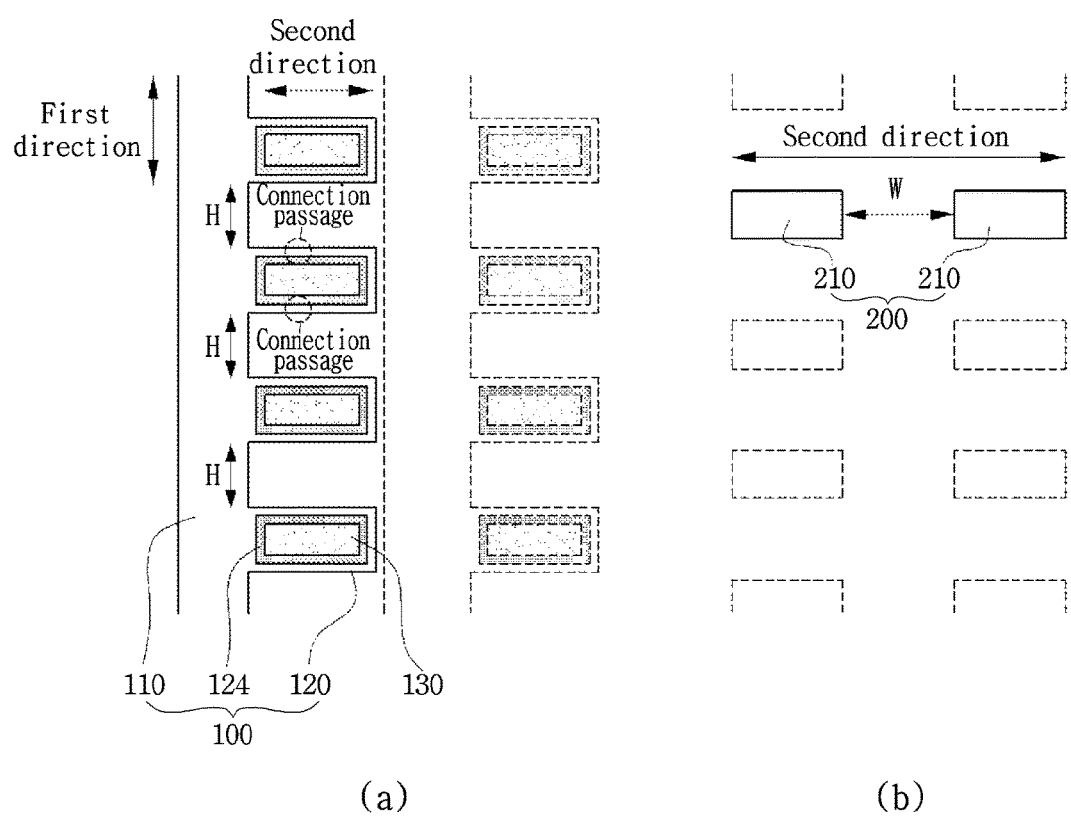
FIG. 2 shows plan views showing in detail the sensing electrode depicted in FIG. 1.

FIG. 1 is a schematic plan view showing a touch panel including an improved sensing electrode according to the first embodiment. FIGS. 2a and 2b are plan views showing in detail the sensing electrode depicted in FIG. 1 and divided into first and second sensing electrodes 100 and 200.

The first sensing electrode 100 may include a plurality of first sensing electrodes. Referring to FIG. 2a, each of the first sensing electrodes 100 may include a main electrode 110 disposed in the first direction (for example, a longitudinal direction). Each of the first sensing electrodes 100 may extend from an edge of the main electrode 110 in the second direction (for example, a traversal direction) and may include a plurality of sub-electrodes 120 in each of which at least one opening part 124 is formed. The sub-electrodes 120 are formed to be spaced apart from each other by a constant interval H for every main electrode 110. In this case, the opening parts 124 may vertically pass through the sub electrodes 120, respectively. Thus, each of the sub-electrodes 120 is provided with a plurality of electrical connecting passages formed along an edge of the opening part 124.

A dummy pattern 130 may be disposed to be adjacent to the sensing electrode part. According to the first embodiment, at least one dummy pattern 130 may be disposed in each opening part 124. The dummy pattern 130 may be formed to have an area less than that of the opening part 124 and to be inwardly spaced apart from the edge of the opening part 124 by a predetermined interval. Thus, the sub-electrode 120 and the dummy pattern 130 may be insulated from each other.

Figure 3:
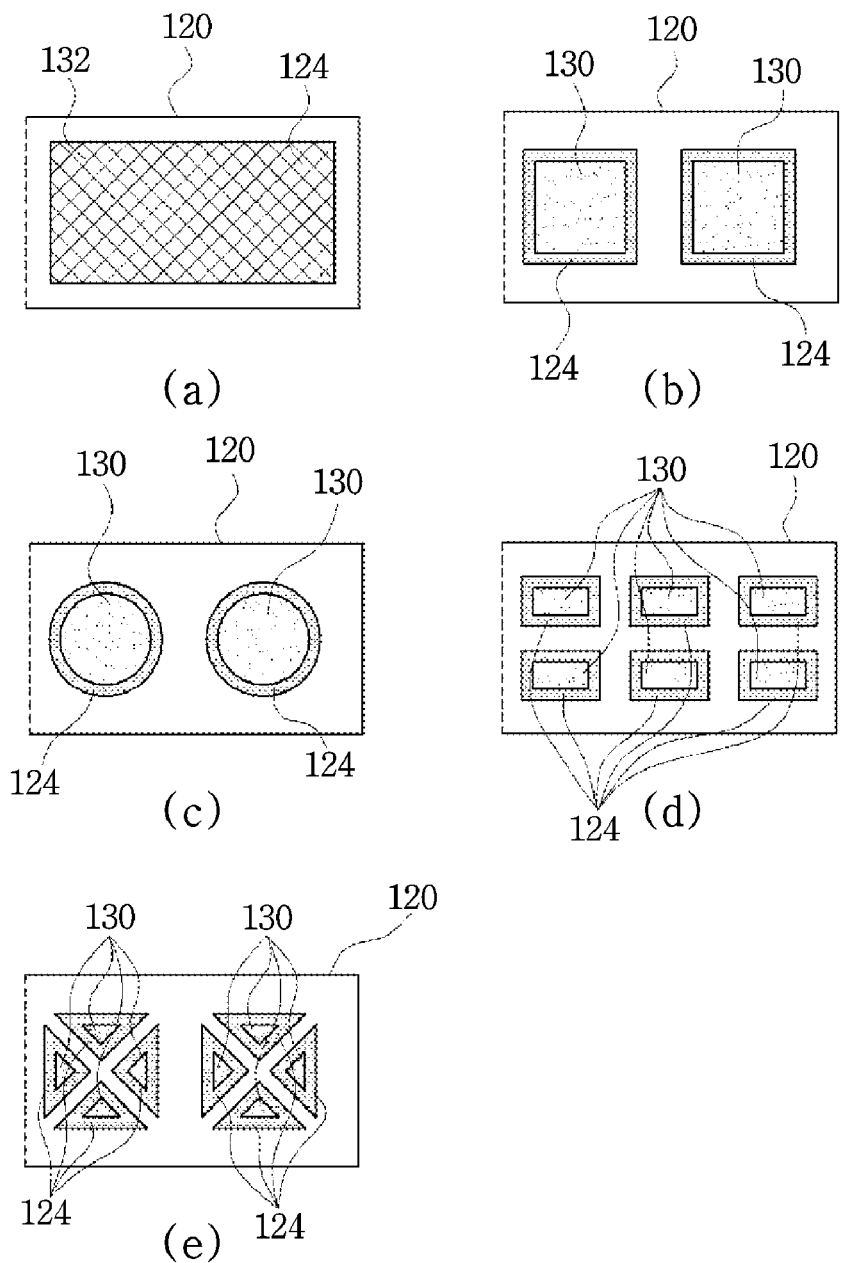
FIG. 3 shows views showing various structures of the sub-electrode of the touch panel according to the first embodiment.

Although one opening part 124 which is formed per one sub-electrode 120 and only one dummy pattern 130 which is disposed inside each of the opening parts 124 are depicted in FIG. 2a, the embodiment is not limited thereto. In addition, the numbers and shapes of the opening parts 124 and the dummy patterns 130 may be various and will be additionally described below with reference to FIG. 3.

As the dummy pattern 130 is disposed in the sub-electrode 120, it may be confirmed through FIG. 2a that the sub-electrode 120 is provided with the plurality of electric connecting passages which allow the sub-electrode 120 to be electrically connected to the main electrode 110. Hereinafter, this will be described in more detail with reference to FIG. 4.

The second sensing electrode 200 may include a plurality of second sensing electrodes 200 and may be spaced apart from the first sensing electrode 100 without any overlapped areas, so that the second sensing electrode 200 is electrically insulated from the first sensing electrode 100. Referring to FIG. 2b, each of the second sensing electrodes 200 includes a plurality of unit electrodes 210 disposed in the second direction (for example, a traversal direction). In this case, the unit electrodes 210 are disposed between mutually adjacent sub-electrodes, respectively, (that is, areas where the constant interval H is formed in FIG. 2a) and are spaced apart from each other by a constant interval W in an area crossing the first sensing electrodes 100 in the second direction.

The first and second sensing electrodes 100 and 200 may be formed by using at least one of various schemes such as an etching scheme, a sputtering scheme, a screen printing scheme, or a photolithography scheme.

The first and second sensing electrodes 100 and 200 may include at least one of indium tin oxide (ITO), carbon nanotube (CNT), indium zinc oxide (IZO), zinc oxide (ZnO), graphene, conductive polymer, silver (Ag) nanowire and copper oxide.

In addition, at least one of the first and second sensing electrodes 100 and 200 may include various metals. For example, the sensing electrode may include at least one of Cr, Ni, Cu, Al, Ag, Mo, Au, Ti and the alloy thereof.

The sensing electrode including at least one metal may be formed in a mesh shape. In detail, the sensing electrode may include a plurality of sub-patterns which are arranged in a mesh shape while crossing each other. Since the sensing electrode has the mesh shape, the pattern of the sensing electrode may not be viewed on an active area, for example, a display area. That is, even though the sensing electrode is formed of metal, the pattern may not be viewed. Even when the sensing electrode is a large size of a touch window, the resistance of the touch window may be reduced.

In addition, the first and second sensing electrodes 100 and 200 may be formed on an upper portion of a transparent substrate 10 formed of at least one of glass, plastic and polyethylene terephthalate (PET). In this case, the first and second sensing electrodes 100 and 200 may be formed on the same one surface of a single transparent substrate 100. Since the first and second sensing electrodes 100 and 200 are formed on the single transparent substrate 100 together, the thickness of the touch panel may be reduced.

Meanwhile, although the first and second sensing electrodes 100 and 200 are depicted in FIGS. 2a and 2b, respectively, this is for the purpose of convenient description and it may be easily understood by those ordinary skilled in the art that the first and second sensing electrodes 100 and 200 are collectively formed through the same process.

In addition, the first and second directions may be variously set to calculate the coordinates of a position to which touch stimulation is applied. Preferably, the first and second directions may be perpendicular to each other.

FIGS. 3a to 3e are views showing various structures of the sub-electrode 120 of the touch panel according to the first embodiment.

First, referring to FIG. 3a, a fine conductive wire 132 having a mesh shape may be formed in the opening part 124 formed in the sub-electrode 120 according to the embodiment. In detail, the opening part 124 may be vertically formed through the sub-electrode 120 except for a predetermined area of an edge of the sub-electrode 120, and the fine conductive wires 132 may cross each other in the opening part 124 in a mesh shape. In this case, the fine conductive wires 132 may be formed of the same material through the same process as the first and second sensing electrodes 100 and 200. The fine conductive wires 132 are electrically connected to the sub-electrode 120, respectively. Thus, even when several of the fine conductive wires 132 are cut off, the electrical connection between the sub-electrode 120 and the main electrode 110 may be maintained through the other fine conductive wires 132.

In addition, referring to FIGS. 3b to 3e, the opening part 124 of the sub-electrode 120 and the dummy pattern 130 disposed in the opening part 124 may have various shapes such as a square shape, a circular shape, a rectangular shape or a triangular shape.

In addition, when the plurality of dummy patterns 130 is disposed in one sub-electrode 120, the dummy patterns 130 may be formed to have the same shape and size. In addition, the dummy patterns 130 may be arranged in a matrix shape. Thus, when outer force is applied to the dummy patterns 130, the shock may be uniformly distributed and in addition, the dummy patterns 130 are allowed not to be easily viewed with naked eye from an outside.

FIG. 4 is a view illustrating the electrical connection of the sub-electrode 120 through another electrical connecting passage when several electrical connecting passages included in the sub-electrode 120 depicted in FIG. 3b are damaged. In detail, referring to FIG. 4a, the sub-electrode 120 may include a first sub-electrode 121 formed at one side (for example, an upper portion) of the opening part 124 in the second direction, a second sub-electrode 122 formed at an opposite side of the opening part in the second direction, and a third sub-electrode 123 formed in the first direction to connect the first and second sub-electrodes 121 and 122 to each other. In this case, the third sub-electrode 123 may be a portion of the sub-electrode 120 except for the first and second sub-electrodes 121 and 122. Thus, the dummy pattern 130 is surrounded by the first to third sub-electrodes 121 to 123.

Referring to FIG. 4b, it may be confirmed that a part of the upper and right side edges is cut off. The disconnecting phenomenon of the sub-electrode 120 may occur due to the outer force applied during a manufacturing process or a daily life, or an error of the manufacturing process.

For example, when the sub-electrode 120 has a bar shape so that the dummy pattern 130 is not disposed therein, only one electrical connecting passage may be formed between the sub-electrode 120 and the main electrode 110. In this case, if the sub-electrode 120 is cut off in the second direction, the touch stimulation applied into the corresponding area is not properly sensed.

To the contrary, since the sub-electrode 120 of the touch panel according to the first embodiment includes the first to third sub-electrodes 121 to 123 for providing the plurality of electrical connecting passages, even though several of the first to third sub-electrodes 121 to 123 are cut off, the sub-electrode 120 is electrically connected to the main electrode 110 through the remaining electrical connecting passages (see the dotted line arrow), so that the touch sensing performance may be maintained.

For example, referring to FIG. 4b, it may be confirmed that a part of the first sub-electrode 121 is cut off and a part of the third sub-electrode 123b disposed at a right side is cut off.

In this case, it may be confirmed that the second sub-electrode 122 is electrically connected to the first sub-electrode 121 through the third sub-electrode 123a disposed at the center.

Meanwhile, although FIG. 4 has been explained while focusing on the sub-electrode 120 depicted in FIG. 3b, the embodiment is not limited thereto. The embodiment may be applied to dummy patterns 130 having various shapes as well as the shapes depicted in FIGS. 3a and 3c to 3e.

Figure 5:
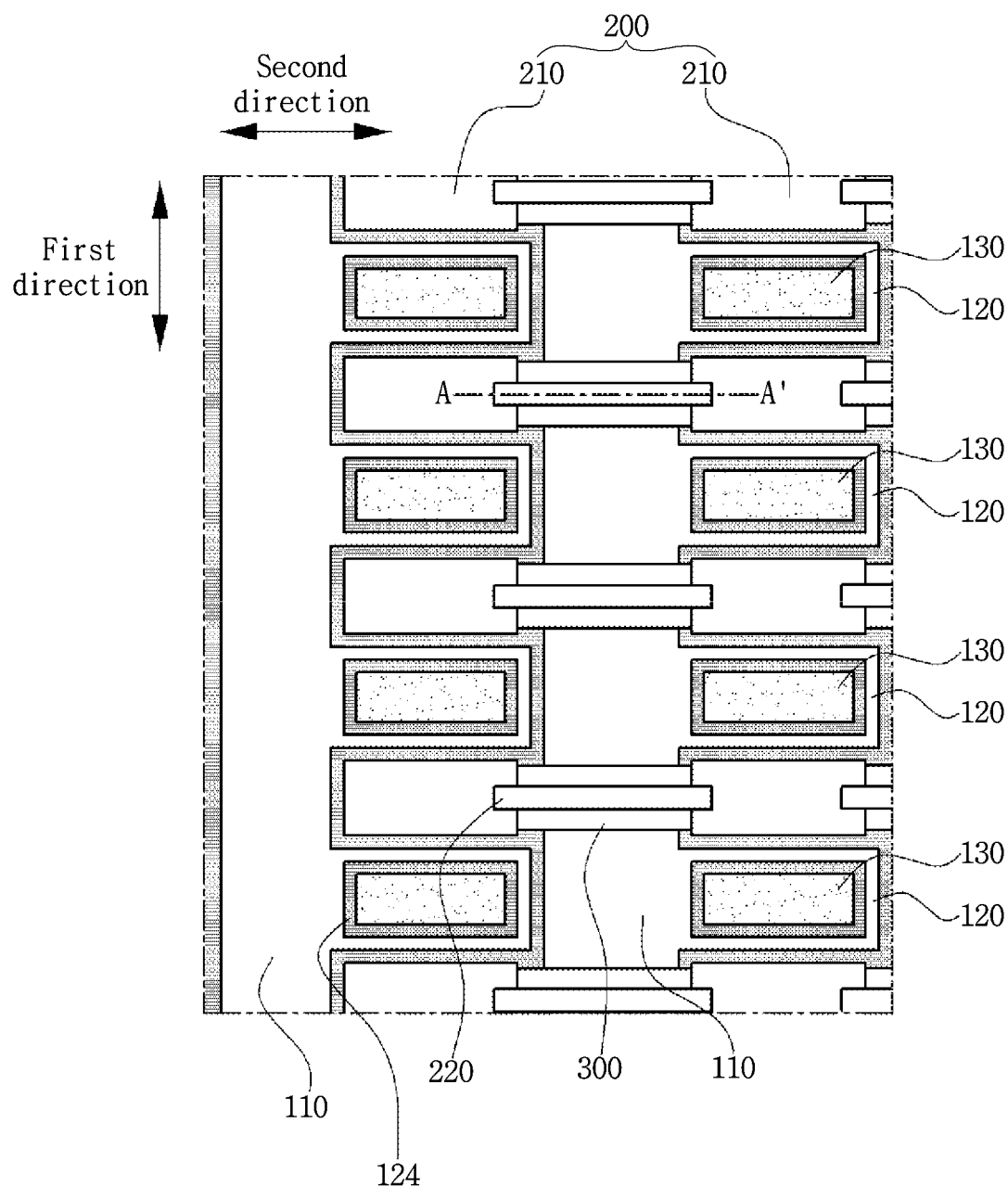
FIG. 5 is a plan view showing an example of a structure of insulating the second sensing electrode of the touch panel depicted FIG. 1 from the first sensing electrode.
Figure 6:
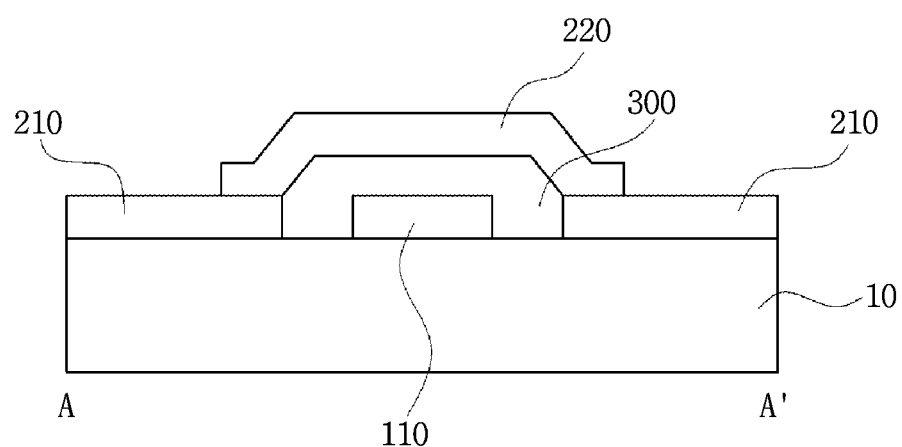
FIG. 6 is a sectional view taken along line A-A' of FIG. 5.

FIG. 5 is a plan view showing an example of a structure of insulating the second sensing electrode 200 of the touch panel depicted FIG. 1 from the first sensing electrode 100. FIG. 6 is a sectional view taken along line A-A' of FIG. 5. In detail, since a plurality of unit electrodes 210 included in each of the second sensing electrodes 200 depicted in FIG. 1 are spaced apart from each other in the second direction so that the unit electrodes 210 are electrically disconnected to each other, FIGS. 5 and 6 show a structure of electrically connecting the unit electrodes 210 included in each of the first sensing electrodes 100 to each other in the second direction.

First, referring to FIG. 5, the touch panel according to the embodiment may further include an insulating part 300, and each second sensing electrode 200 may further include a bridge part 220.

The insulating part 300 may be formed in an intersection area between the first and second sensing electrodes 100 and 200. In detail, the intersection area between the first and second sensing electrodes 100 and 200 is a part of the main electrode 110 interposed between a pair of unit electrodes 210 adjacent to each other in the second direction. In this case, as shown in FIG. 6, the insulating part 300 may be formed to coat the entire part (that is, upper and side surfaces) of the main electrode 110 placed in the intersection area between the first and second sensing electrodes 100 and 200.

The bridge part 220 is formed on an upper portion of the insulating part 300 and parts of both ends of the bridge part 220 are connected to the unit electrodes 210, respectively, such that the second sensing electrode 200 is insulated from the first sensing electrode 100. The bridge part 220 allows the pair of unit electrodes 210 adjacent to each other in the second direction to be electrically connected to each other.

Meanwhile, similarly to the first and second sensing electrodes 100 and 200, the bridge part 220 may include at least one of indium tin oxide (ITO), carbon nanotube (CNT), indium zinc oxide (IZO), zinc oxide (ZnO), graphene, conductive polymer, silver (Ag) nanowire and copper oxide.

In addition, the bridge part 220 may include various metals. For example, the bridge part 220 may include at least one of Cr, Ni, Cu, Al, Ag, Mo, Au, Ti and the alloy thereof.

In addition, since the insulating part 300 and the bridge part 220 are formed in an area in which adjacent unit electrodes 210 are spaced apart from each other in the second direction, when the number of unit electrodes 210 included in one second sensing electrode 200 is equal to N, each number of the insulating parts 300 and the bridge parts 220 required to electrically connect the second sensing electrodes 200 to each other may be equal to (N−1).

Figure 7:
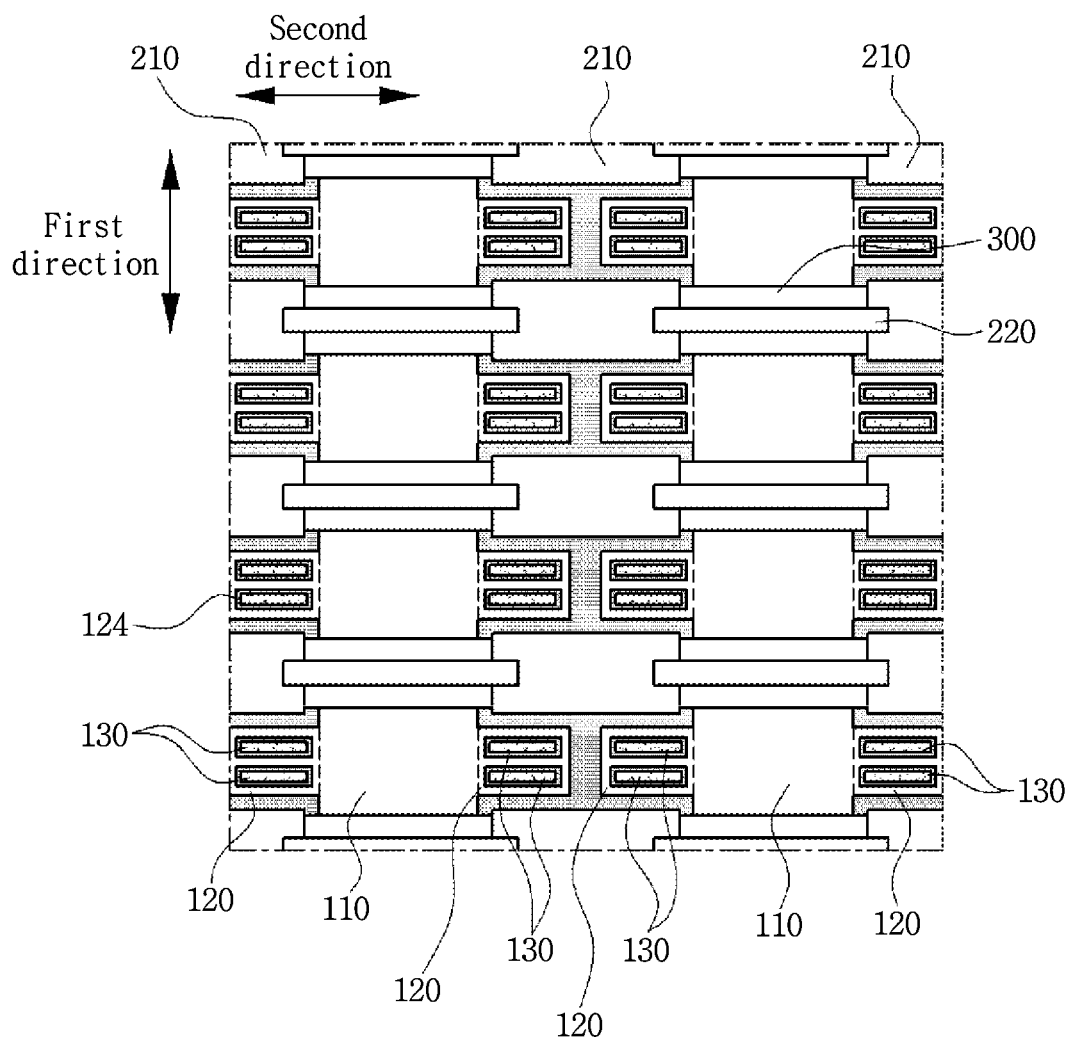
FIG. 7 is a schematic plan view showing a touch panel including an improved sensing electrode according to another embodiment.

FIG. 7 is a schematic plan view showing a touch panel including an improved sensing electrode according to another embodiment. The sensing electrode depicted in FIG. 7 is to illustrate that the shape of the sensing electrode described above with reference to FIGS. 1 and 5 may be modified. That is, although the sub-electrodes 120 extending in the second direction (for example, the traversal direction) from only 'one side edge (right or left edge)' of the main electrode 110 have been depicted in FIGS. 1 and 5, the embodiment is not limited thereto and may be variously modified. FIG. 7 is for illustrating one example only. In detail, referring to FIG. 7, it may be confirmed that the sensing electrode of FIG. 7 is different from those of FIGS. 1 and 5 because the sub-electrode 120 extends in the second direction from 'both side edges' of the main electrode 110.

Hereinafter, a touch panel according to the second embodiment will be described with reference to FIGS. 8 to 13. In this case, the features, structures and effect proposed in the first embodiment may be incorporated or modified in the second embodiment by those ordinary skilled in the art.

Figure 8:
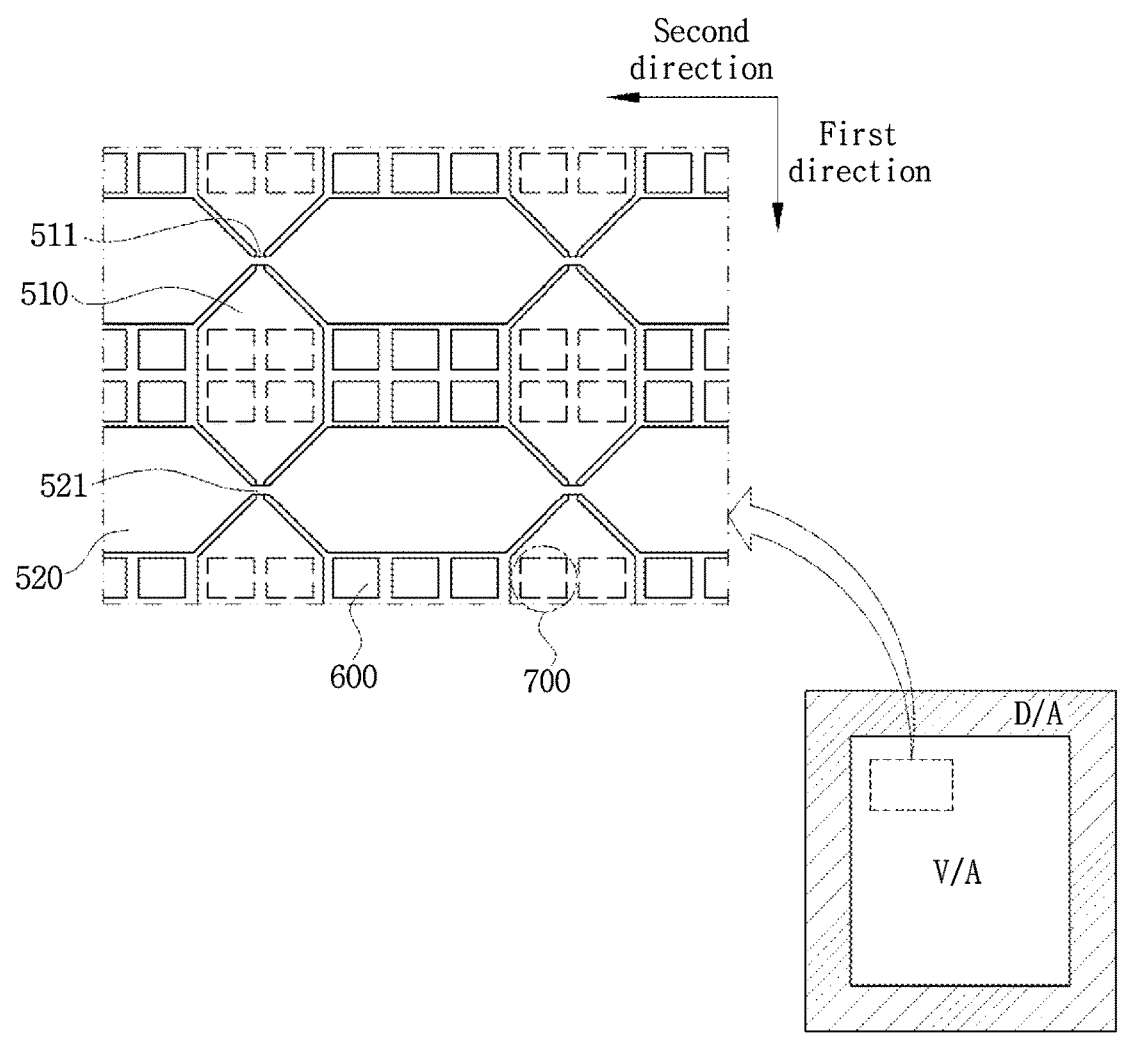
FIG. 8 is a plan view showing a touch panel according to the second embodiment.
Figure 10:
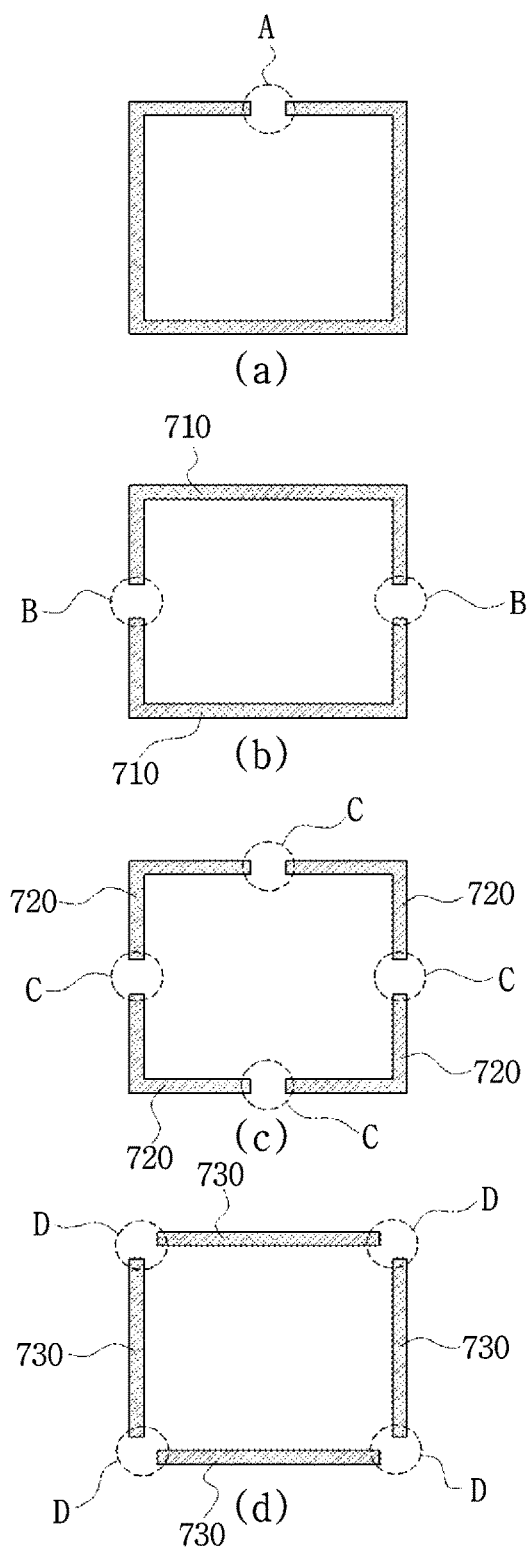
FIG. 10 shows views of various shapes of the first opening part 700 of the touch panel according to the second embodiment.

FIG. 8 is a plan view showing a touch panel according to the second embodiment. FIGS. 9a to 9c are plan views illustrating in detail the arrangement of the sensing electrode part and dummy pattern depicted in FIG. 8.

First, referring to FIG. 8, the touch panel according to the second embodiment may include a substrate, a sensing electrode part, a dummy pattern 200 and a first opening part 300.

The sensing electrode part may include first and second sensing electrodes 510 and 520.

The substrate may include at least one of various materials, such as polyethylene terephthalate (PET), polycarbonate (PC), polyether sulfone (PES), polyimide (PI), polymethyl methacrylate (PMMA), glass, etc., which may be coated with a material used for forming the sensing electrode part.

The sensing electrode part is formed in a touch active area on the substrate and configured to sense a touch signal by a person or an object. In the embodiment, the touch active region signifies an area through which an instruction may be input by using a touch signal. In addition, a touch inactive area, which has the concept opposite to that of the touch active area, is not activated even if a user touches the dead area, so the touch inactive area signifies an area through which any touch instructions cannot be input.

In this case, the touch active area may be equal to the view area V/A described above, but the embodiment is not limited thereto. It should be understood that the touch active area signifies an area which includes a part or all of the dead area D/A as well as a part or all of the view area V/A.

Such a sensing electrode part may be formed of conductive polymer. In detail, the sensing electrode part may be formed of polyaniline, polyacetylene or polyphenylene vinylene. In addition, a material, such as indium-tin oxide (ITO), an organic transparent electrode material including a carbon nanotube, graphene, zinc oxide (ZnO) and tin oxide (SnO2), etc., may be used to form the sensing electrode part. Further, it is obvious to those ordinary skilled in the art that transparent electrodes of various materials may be selectively used for the sensing electrode.

Meanwhile, the dummy pattern 600 may be adjacent to the sensing electrode part. According to the second embodiment, the dummy pattern 600 may be disposed outside the sensing electrode part.

In detail, an area, in which the sensing electrode part is not formed in the view area V/A, may be interposed between the adjacent sensing electrode parts. In more detail, the view area V/A may be greatly divided into a sensing electrode formed area and a sensing electrode unformed area, where the sensing electrode unformed area (hereinafter, referred to as a dummy area) has a light transmittance and refractive index different from those of the sensing electrode formed area, so that the visibility of the touch panel may be deteriorated. To compensate the differences of the transmittance and refractive index according to whether the sensing electrode part exists or not, the touch panel according to the second embodiment may include a dummy pattern 600 formed in the dummy area.

The dummy pattern 600 may be formed of a non-conductive material having a light transmittance and refractive index similar to those of the sensing electrode part, but the embodiment is not limited thereto. The dummy pattern 600 may be formed of the same material as the sensing electrode part. When the dummy pattern 600 is formed of the same material as the sensing electrode part, as shown in FIG. 8, the sensing electrode part and the dummy pattern 600 may be spaced apart from each other by a predetermined interval in order to prevent the dummy pattern 600 from making electrical contact with the sensing electrode part.

The first opening part 700 is disposed inside the sensing electrode part to improve the visibility of the touch panel. In detail, the first opening part 700 may have a shape of surrounding an area of the sensing electrode part and may include at least one opening part to electrically connect the surrounded area to the remaining area.

The sensing electrode part, the dummy pattern 600 and the first opening part 700 may be formed on a substrate. The embodiment does not specifically limit the substrate if the substrate has a predetermined strength. For example, the substrate may be formed of polyethylene terephthalate (PET), polycarbonate (PC), polymethyl methacrylate (PMMA), polyethylene naphthalate (PEN), polyether sulfone (PES), cyclic olefin polymer (COC), a triacetylcellulose (TAO) film, a polyvinyl alcohol (PVA) film, a polyimide (PI) film, polystyrene (PS), glass, tempered glass, etc.

The sensing electrode part of the touch panel according to the embodiment may include first and second sensing electrodes 510 and 520. Referring to FIGS. 9a to 9c, it may be confirmed that the first and second sensing electrodes 510 and 520 and the dummy pattern 600 of the touch panel depicted in FIG. 8 are shown in detail while being separated from each other. The first and second sensing electrodes 510 and 520 may be formed through various schemes such as an etching scheme, a photolithography scheme, a sputtering scheme, a screen printing scheme, etc.

The dummy patterns 600 may be formed in each dummy area surrounded by the first and second sensing electrodes 510 and 520. Referring to FIGS. 1 and 2a, six dummy patterns 600 having a rectangular shape are aligned in a matrix of 2×3 in each dummy area, but this is for the purpose of convenient explanation and the shape, size and number of the dummy patterns 600 are not limited thereto.

Referring to FIGS. 9b and 9c, the first sensing electrode 510 may be formed in the first direction (for example, a longitudinal direction) and the second sensing electrode 520 may be formed in the second direction (for example, a traversal direction). In detail, the first sensing electrodes 510 may be formed in the first direction while being interconnected to each other through the first connecting part 511. The second sensing electrodes 520 may be formed in the second direction while being interconnected to each other through the second connecting part 521. The first and second sensing electrodes 510 and 520 may perform the functions of driving and sensing electrodes Tx and Rx. For example, if the first sensing electrode 510 performs the function of the driving electrode Tx, the second electrode 520 performs the function of the sensing electrode Rx. To the contrary, if the first sensing electrode 510 performs the function of the sensing electrode Rx, the second electrode 520 performs the function of the driving electrode Tx.

In this case, an insulating part may be formed at an intersection area between the first and second sensing electrodes 510 and 520, that is, at an intersection area between the first and second connecting parts 511 and 521 to insulate the first and second sensing electrodes 510 and 520 from each other.

The first opening part 700 may be disposed inside one of the first and second sensing electrodes 510 and 520. The first opening part 700 disposed only inside the first sensing electrode 510 is depicted in FIGS. 8 and 9a, but to the contrary, the opening part 700 may be disposed only inside the second sensing electrode 520.

Thus, the dummy patterns 600 formed in the dummy area are disposed to alternate with the first or second sensing electrode 510 or 520, so that the visibility of the touch panel is primarily improved due to the regularity. Further, the regularity according to the shape of the sensing electrode part and the dummy pattern 600 is compensated for by the first opening part 700 disposed inside one of the first and second sensing electrodes 510 and 520, so that the visibility of the touch panel may be secondarily improved.

In this case, an area of the sensing electrode surrounded by the first opening part 700 may be formed corresponding to the shape and size of the dummy pattern 600. Hereinafter, it will be described in more detail with reference to FIGS. 10 to 12.

FIGS. 10a to 10d are views showing various shapes of the first opening part 700 of the touch panel according to the embodiment.

First, referring to FIG. 10a, the first opening part 700 may be formed in a continuous shape except for only one opening part A. The area of the sensing electrode surrounded by the first opening part 700 is electrically connected to an outer area thereof through the opening part A.

Meanwhile, differently from the first opening part 700 depicted in FIG. 10a, the first opening parts 700 depicted in FIGS. 10b to 10d may include a plurality of sub-patterns.

Referring to FIG. 10b, the first opening part 700 may include two sub-patterns 710. It may be confirmed that the two sub-patterns 710 are spaced apart from each other at left and right sides, so that two opening parts B are formed. The area of the sensing electrode surrounded by the first opening part 700 is electrically connected to an outer area thereof through the opening parts B.

Then, referring to FIG. 10c, the first opening part 700 may include four sub-patterns 720. It may be confirmed that the four sub-patterns 720 are spaced apart from each other at upper, lower, left and right sides, so that four opening parts C are formed. The area of the sensing electrode surrounded by the first opening part 700 is electrically connected to an outer area thereof through the opening parts C.

In addition, referring to FIG. 10d, the first opening part 700 including four sub-patterns 730 is similar to that of FIG. 10c, but the first opening part 700 is different from that of FIG. 10c in that the sub-patterns are spaced apart from each other at each vertex area of the four sub-patterns 730 having the rectangular shape. The four sub-patterns 730 are spaced apart from each other at each vertex area, so that four opening parts D are formed and the area of the sensing electrode surrounded by the first opening part 700 is electrically connected to an outer area thereof through the opening parts D.

Meanwhile, the shape of the first opening part 700 describe above is not limited to the shapes depicted in FIGS. 10a to 10d. It may be understood by those ordinary skilled in the art that, as well as the number and position of the sub-patterns, the positions and number of open areas formed by the sub-patterns may be variously modified.

The first opening part 700 may be disposed inside the sensing electrode part and may open at least a part of the sensing electrode to expose the substrate. In detail, an area for forming the first opening part 700 is emptied in advance through a sputtering or screen printing scheme when the sensing electrode part is formed, or a part of the sensing electrode is remove through an etching or photolithography scheme after forming the sensing electrode, so that the first opening part may be formed.

Figure 11:
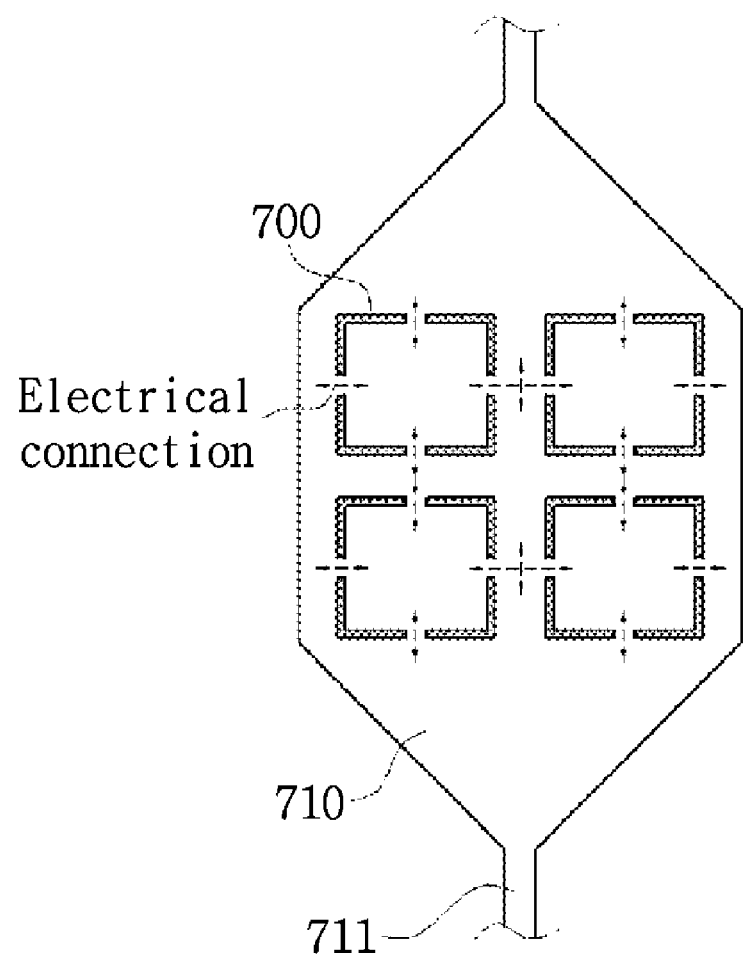
FIG. 11 is a view showing an electrical connection of the sensing electrode through the first opening part of the touch panel according to the second embodiment.

FIG. 11 is a view showing an electrical connection of the sensing electrode through the first opening part 700 of the touch panel according to the embodiment.

Referring to FIG. 11, the first opening part 700 disposed inside the first sensing electrode 510 of the touch panel according to the second embodiment may be confirmed. Although four opening parts 700 aligned in a matrix of 2×2 inside each sensing electrode 510 are depicted in FIGS. 8, 9 and 11, this is for the purpose of convenient explanation and the number and disposition form of the first opening part 700 disposed inside each of the first sensing electrodes 510 may be various. In addition, the first opening part 700 may be formed in not the first sensing electrode 510 but the second sensing electrode 520.

In detail, the first opening part 700 according to the second embodiment has a start point and an end point which are spaced apart from each other, so that the area of the sensing electrode surrounded by the first opening part 700 may not be insulated from but electrically connected to the outer area thereof. Thus, the electric signal applied from a circuit of the touch panel may be transmitted to all areas of each sensing electrode part except for the first opening part 700 as arrows depicted in FIG. 11.

FIGS. 12a and 12b are views illustrating the comparison of the dummy pattern 600 and the first opening part 700 in the touch panel according to the embodiment.

First, referring to FIG. 12a, the dummy pattern 600 having a rectangular shape is depicted at the left side of FIG. 12a and the first opening part 700 which opens upper, lower, left and right portions of the sensing electrode part while surrounding an area of the sensing electrode part is depicted at the right side of FIG. 12a. Each dummy pattern 600 may have a square shape having a width P1 equal to a height H2, but the embodiment is not limited thereto.

Since it is preferable that the shape and size of the first opening part 700 correspond to the dummy pattern 600 in order to improve the visibility of the touch panel, the first opening part 700 may be formed such that the area (P2×H2) of each area surrounded by the first opening part 700 is 0.9 to 1.1 times of an area (P1×H1) of each dummy pattern 600. In addition, the ratio of the width P2 and height H2 of the first opening part 700 to the width P1 and height H1 of the dummy pattern 600 may be equal to '0.9~1.1':1.

Next, referring to FIG. 12b, the dummy pattern 600 of a circular shape having a first radius R1 is depicted at the left side of FIG. 12b, and the first opening part 700 provided at upper and lower portions thereof with opening parts E while surrounding an area of the sensing electrode in a circular shape having a second radius R2 is depicted at the right side of FIG. 12b. In this case, the first opening part 700 is preferably formed such that the relationship between an area surrounded by the first opening part 700 and an area of the dummy pattern 600 satisfies $\pi R2^2:\pi R1^2 =$ '0.9~1.1':1.

That is, if the area surrounded by the first opening part 700 is less or greater than the area of each dummy pattern 600 beyond a predetermined range, the regularity by the sensing electrode and dummy pattern 600 formed on the transparent substrate 10 is reduced, so that there is a limit to sufficiently improve the visibility of the touch panel. Thus, it is preferable that the first opening part 700 is formed such that the ratio of the area surrounded by the first opening part 700 to the area of each dummy pattern 600 is within the predetermined range.

In addition, a width W1 of the first opening part 700 depicted in FIG. 12a and a width W2 of the first opening part 700 depicted in FIG. 5b may be formed within a preset range, and preferably, may be in the range of 20 μm to 50 μm. When the width of the first opening part 700 is less than 20 μm, the width of the opening part is excessively smaller than the entire width of the sensing electrode, so that the improvement of visibility through the formation of the opening part may be lowered. When the width of the first opening part 700 exceeds 50 μm, the ratio of the opening part in the sensing electrode is excessively increased, so that the sensing performance against touch stimulation may be deteriorated.

Figure 13:
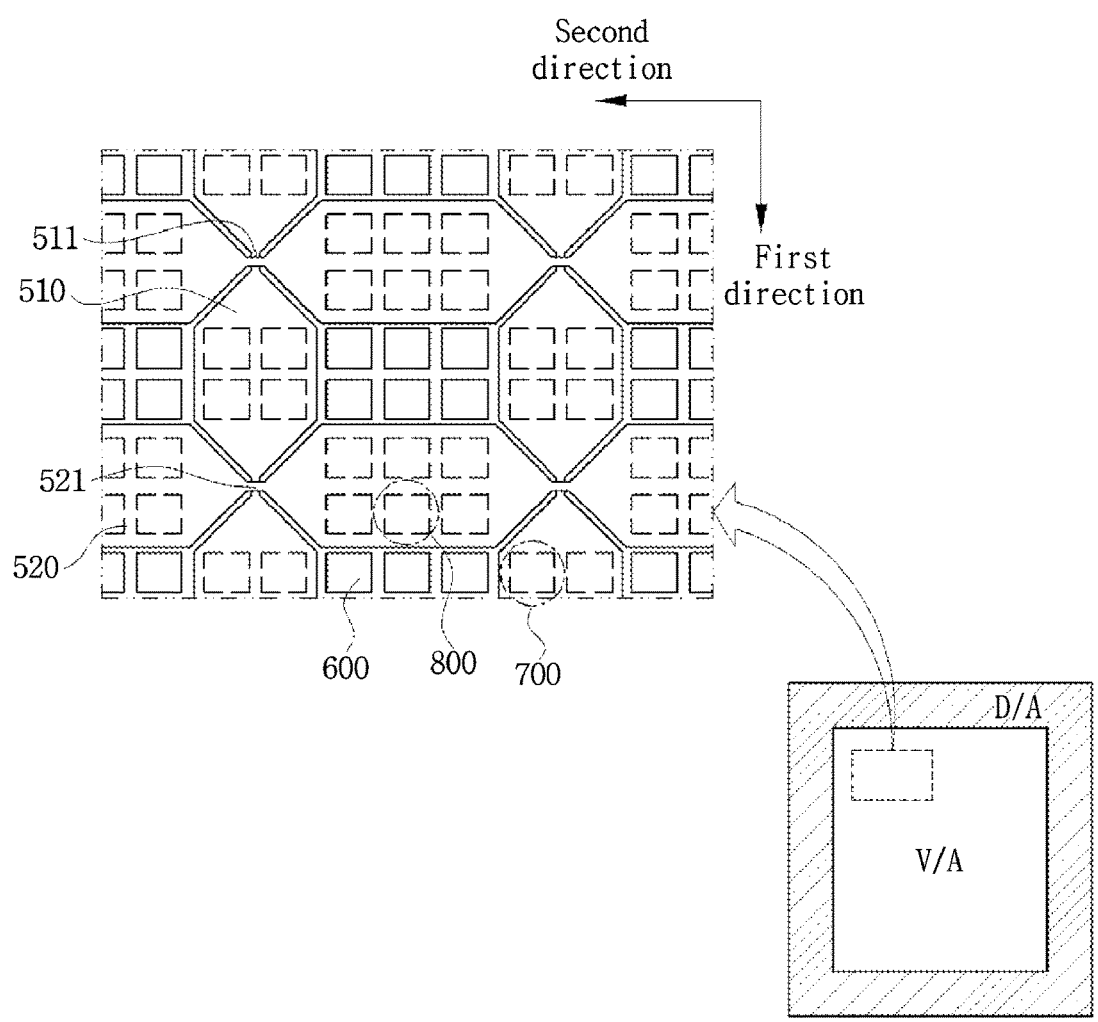
FIG. 13 is a plan view of a touch panel according to another embodiment.

FIG. 13 is a plan view of a touch panel according to another embodiment.

Referring to FIG. 13, when compared with the touch panel described with reference to FIGS. 8 and 9, the touch panel according to another embodiment includes opening parts which are formed in both of the first and second sensing electrodes 510 and 520. That is, differently from the second embodiment in which the first opening part 700 is formed only in the first sensing electrode 510, the second opening part 800 is formed in the second sensing electrode 520, so that the regularity may be improved due to the arrangement of the dummy pattern 600 crossing the sensing electrode part. Thus, variation of the light transmittance and refractive index may be more attenuated.

In detail, referring to FIG. 13, it may be confirmed that six second opening parts 800 are aligned in a matrix of 2×3 inside the second sensing electrode 520. It is preferable that the second opening part 800 is formed such that the area surrounded by the second opening part 800 is 0.9 to 1.1 times of the area of each dummy pattern 600.

In addition, the second opening part 800 may have the same shape, size and width as the first opening part 700, but it may be changed according to a situation.

Meanwhile, it should be understood that the number and arrangement of the second sensing electrodes 520 are not limited to those of FIG. 13 and may vary depending on the application or size of the touch panel.

Figure 14:
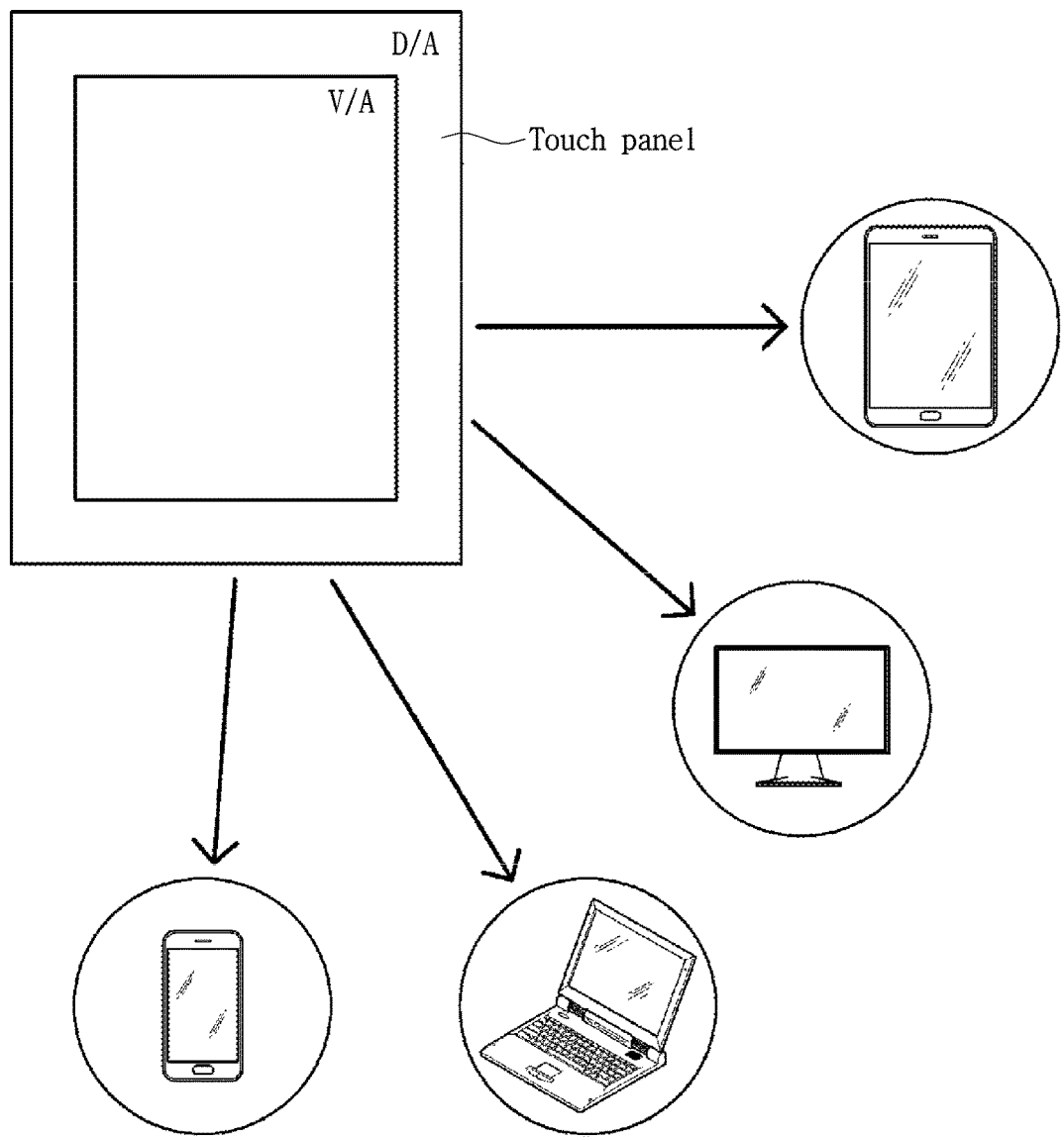
FIGS. 14 to 16 are views showing image display devices to which a touch panel according to the embodiment may be installed.
Figure 15:
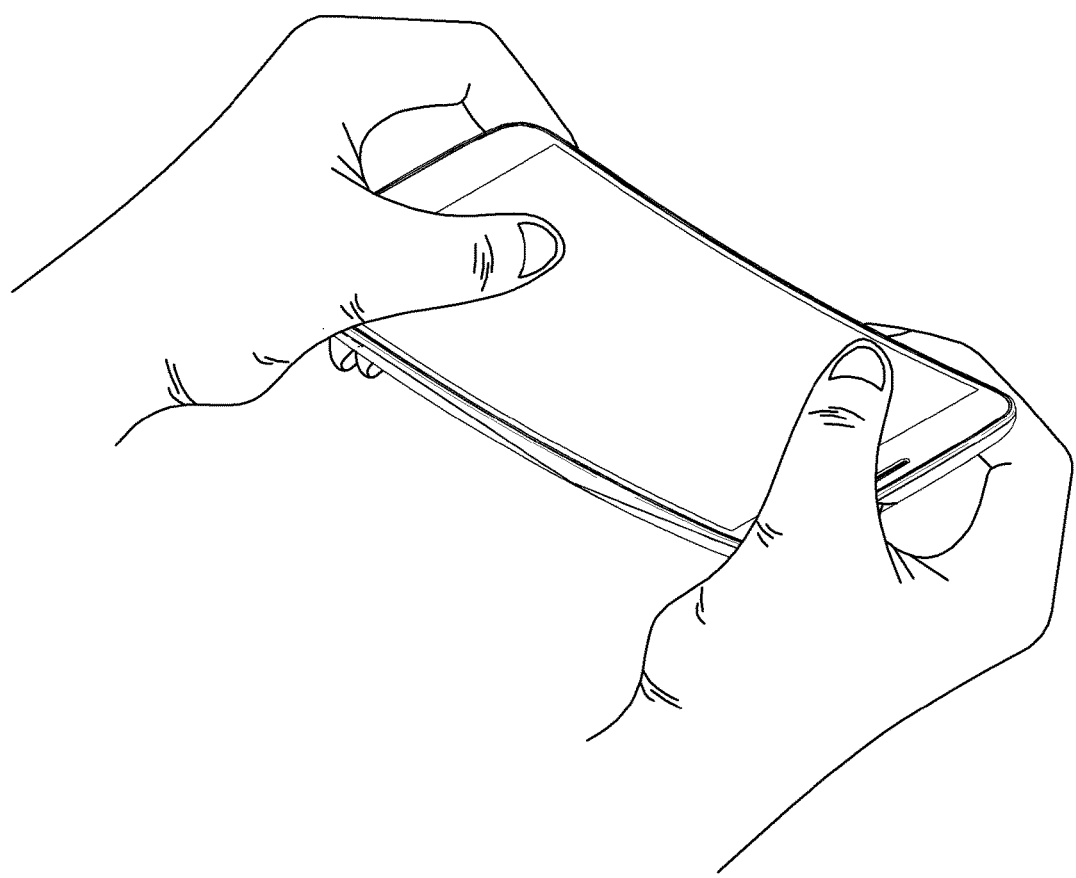
Figure 16:
Figure 17:
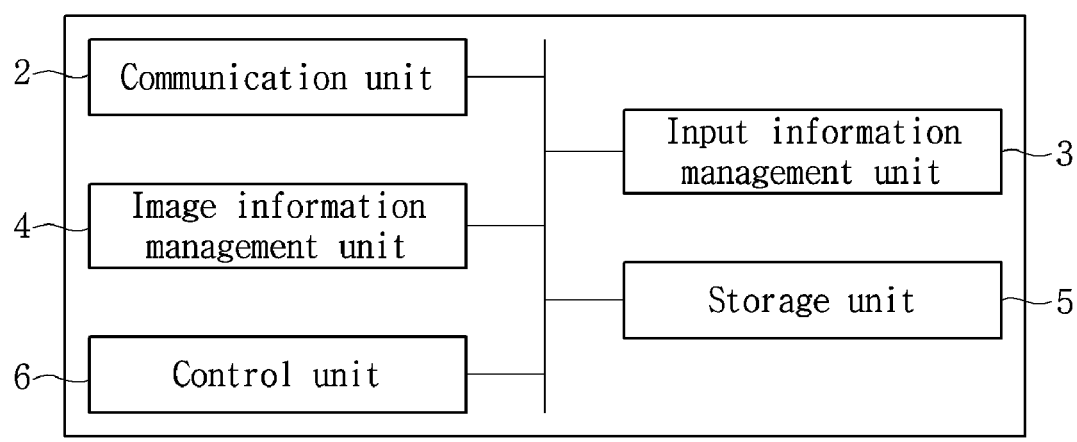
FIG. 17 is a view showing an exemplary configuration of an image display device according to the embodiment.

FIGS. 14 to 16 are views showing image display devices to which a touch panel according to the embodiment may be installed. FIG. 17 is a view showing an exemplary configuration of an image display device according to the embodiment.

The touch panel according to the embodiment described above may be applied to various image display devices as shown in FIG. 14. For example, the touch panel according to the present disclosure may be applied to a mobile image display device such as a smart phone, a tablet, a PDA, a laptop computer, a digital camera, etc., and in addition, may be applied to various image display devices such as a smart TV, a PC, a digital frame, a navigation device, etc. That is, the touch panel according to an embodiment may process touch input information and may be applied to various image display devices for displaying image information.

As shown in FIG. 15, the touch panel may include a flexible touch panel bendable. Thus, an image display device including the flexible touch panel may include a flexible image display device. Therefore, a user may bend the image display device with a hand. The flexible touch panel may be applied to a wearable touch device.

Referring to FIG. 16, the touch panel may be applied to a vehicle navigation system as well as an image display device such as a mobile terminal.

Referring to FIG. 17, there are illustrated exemplary elements included in the image display device to which the touch panel according to the embodiment is installed.

In detail, an image display device, in which a touch panel is installed according to the embodiment, includes a communication unit 2 for transmitting/receiving data, an input information management unit 3 for managing information input through the touch panel, an image information management unit 4 for managing information about an image displayed through the touch panel, a storage unit 5 for storing various information concerned with an operation of the image display device, and a control unit 6 for controlling operations of the communication unit, the input information management unit and the image information management unit. In addition, the image display device may include various elements as well as the above-described elements.

In addition, each element may be implemented only with hardware or software, or may be implemented by a combination of various hardware and software for performing the same function(s). Further, two elements or more may be implemented with one piece of hardware or software, or one element may be implemented with at least two pieces of hardware or software.

The embodiment provides a touch panel which includes a sensing electrode having an improved structure so that the touch panel may maintain touch sensing performance even when the sensing electrode is damaged due to the external force applied during a manufacturing process and a daily life.

In addition, the embodiment provides a touch panel which includes a sensing electrode having an improved structure so that the visibility of the touch panel may be improved.

A touch panel may include: a sensing electrode part including a plurality of first sensing electrodes and a plurality of second sensing electrodes insulated from the first sensing electrodes and crossing the first sensing electrodes; an opening part in the sensing electrode part; and a dummy pattern adjacent to the sensing electrode part.

A touch panel may include: a plurality of first sensing electrodes and a plurality of second sensing electrodes, wherein each of the first sensing electrodes includes: a main electrode extending in a first direction; and a plurality of sub-electrodes extending in a second direction from the main electrode and each having at least one opening part.

The first sensing electrodes and the second sensing electrodes may be formed on a same surface of a single transparent substrate.

The second sensing electrode may be interposed between every two adjacent sub-electrodes.

The first and second sensing electrodes may include at least one of indium tin oxide (ITO), carbon nanotube (CNT), indium zinc oxide (IZO), zinc oxide (ZnO), graphene, conductive polymer, silver (Ag) nanowire and copper oxide.

The touch panel may further include a dummy pattern formed in and spaced apart from each opening part.

The opening part may be provided with a plurality of fine conductive wires may crossing each other to form a mesh shape.

The sub-electrode may include: a first sub-electrode extending in the second direction from one side of the opening part; a second sub-electrode extending in the second direction from an opposite side of the opening part; and a third sub-electrode extending in the first direction to connect the first and second sub-electrodes to each other.

The dummy patterns may be formed to have a same shape and size.

The touch panel may further include an insulating part disposed in an intersection area between the first sensing electrode and the second sensing electrode, wherein each of the second sensing electrodes includes: a plurality of unit electrodes extending in a second direction while being spaced apart from each other in an area in which the unit electrodes cross the main electrode; and a bridge part formed on the insulating part such that the bridge part is insulated from the first sensing electrode, the bridge part electrically connecting a pair of the unit electrodes adjacent in the second direction to each other.

A touch panel may include: a substrate; a sensing electrode disposed on the substrate to sense a touch signal; a dummy pattern disposed outside the sensing electrode; and an opening part disposed in the sensing electrode.

The sensing electrode may include a plurality of first sensing electrodes extending in the first direction; and a plurality of second sensing electrodes extending in the second direction while being insulated from the first sensing electrodes. Further, the opening part may be disposed in at least one of the first sensing electrodes or the second sensing electrodes.

The opening part may be disposed in the sensing electrode part and opens at least a part of the sensing electrode part to expose a substrate.

The opening part may be configured such that a shape of an area surrounded by the opening part corresponds to a shape of the dummy pattern.

The opening part may be configured such that an area surrounded by the opening part is 0.9 to 1.1 times of an area of the dummy pattern.

The opening part may have a width in a range of 20 μm to 50 μm.

The opening part may include a plurality of sub-patterns spaced apart from each other.

An inner area surrounded by the opening part and an outer area may be electrically connected to each other by an area spaced between the sub-patterns.

The dummy pattern may be formed of the same material as the sensing electrode.

According to the embodiments, even though the sensing electrode is damaged by external force applied during a manufacturing process or a daily life, the touch sensing performance may be maintained by improving a structure of the sensing electrode formed in the touch panel. Since the dummy pattern is formed inside the sensing electrode extending in an arbitrary direction (for example, a longitudinal direction, a traversal direction, diagonal direction, etc.) according to the embodiment, the plurality of electrical connection passages may be provided so that, even when one electrical connection passage is cut off, the touch sensing performance may be maintained through the remaining electrical connection passage.

In addition, according to the embodiment, since the dummy pattern may be formed by a process equal to a process of forming a sensing electrode, any additional process is not requested so that the producing cost and manufacturing time of the touch panel may be reduced.

According to the embodiment, the dummy pattern may be formed in the dummy area and the opening part is formed in the sensing electrode, so that the visibility of the touch panel may be improved.

In addition, when the opening part may be formed in the sensing electrode, the area surrounded by the opening part is connected to the remaining area, so that the touch sensing performance of the sensing electrode may be prevented from be deteriorated by the opening part.

Although the embodiment is proposed during a procedure of improving an electrode pad structure of a touch panel, the embodiment is not limited to a touch panel itself and may be applied to any image display devices by those ordinary skilled in the art that the embodiment.

The terms "first", "second" and the like are used only to distinguish one element to another element, but features such as a sequence between elements are not limited to such terms.

Any reference in this specification to "one embodiment," "an embodiment," "example embodiment," etc., means that a particular feature, structure, or characteristic described in connection with the embodiment is included in at least one embodiment of the disclosure. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A touch panel comprising:
 a sensing electrode including a plurality of first sensing electrodes and a plurality of second sensing electrodes insulated from the first sensing electrodes and crossing the first sensing electrodes;
 at least one opening pattern provided in the sensing electrode, wherein the at least one opening pattern includes an arrangement of at least one sub-pattern to separate a first area from a second area, the first area being inside the arrangement of the at least one sub-pattern, and the second area being outside the arrangement of the at least one sub-pattern, and the first area being electrically connected to the second area.

2. The touch panel of claim 1, wherein each of the first sensing electrodes includes:
 a main electrode extending in a first direction; and
 a plurality of sub-electrodes extending in a second direction from the main electrode, and
 a plurality of openings provided in the sub-electrodes such that a separate opening is provided in each separate one of the sub-electrodes.

3. The touch panel of claim 1, wherein the first sensing electrodes and the second sensing electrodes are formed on a same surface of a single transparent substrate.

4. The touch panel of claim 3, wherein a corresponding second sensing electrode is interposed between every two adjacent sub-electrodes.

5. The touch panel of claim 1, wherein the sensing electrode includes at least one of indium tin oxide (ITO), carbon nanotube (CNT), indium zinc oxide (IZO), zinc oxide (ZnO), graphene, conductive polymer, silver (Ag) nanowire or copper oxide.

6. The touch panel of claim 2, wherein a dummy pattern is disposed in at least one of the openings.

7. The touch panel of claim 6, wherein the dummy pattern includes a plurality of fine conductive wires crossing each other to form a mesh shape.

8. The touch panel of claim 2, wherein each of the sub-electrodes includes:
 a first sub-electrode extending in the second direction along a first side of the corresponding opening;
 a second sub-electrode extending in the second direction along a second side of the corresponding opening, wherein the second side is opposite to the first side; and
 a third sub-electrode extending in the first direction to connect the first sub-electrode to the second sub-electrode.

9. The touch panel of claim 6, wherein a plurality of dummy patterns are provided in the plurality of openings, and the dummy patterns and the openings have a same shape and size.

10. The touch panel of claim 3, further comprising an insulator provided in an intersection area between the first sensing electrodes and the second sensing electrodes,
 wherein each of the second sensing electrodes includes:
 a plurality of unit electrodes extending in a second direction while being spaced apart from each other in an area in which the unit electrodes cross the first electrode; and
 a bridge formed on the insulator such that the bridge is insulated from the first sensing electrode, the bridge electrically connecting a pair of adjacent unit electrodes in the second direction to each other.

11. The touch panel of claim 1, comprising a dummy pattern is disposed outside the sensing electrode.

12. The touch panel of claim 11, wherein
the plurality of first sensing electrodes extends in the first direction; and
the plurality of second sensing electrodes extending in the second direction while being insulated from the first sensing electrodes, and
the at least one opening pattern is provided in at least one of the first sensing electrodes or the second sensing electrodes.

13. The touch panel of claim 11, wherein the at least one opening pattern exposes a substrate.

14. The touch panel of claim 11, wherein a shape of an area surrounded by the at least one opening pattern corresponds to a shape of the dummy pattern.

15. The touch panel of claim 11, wherein an area surrounded by the at least one opening pattern is 0.9 to 1.1 times of an area of the dummy pattern.

16. The touch panel of claim 11, wherein the at least one opening pattern has a width in a range of 20 μm to 50 μm.

17. The touch panel of claim 1, wherein the opening pattern includes an arrangement of a plurality of sub-patterns.

18. The touch panel of claim 11, wherein the dummy pattern is formed of a same material as the sensing electrode.

19. The touch panel of claim 1, wherein the first area is part of the sensing electrode, and the second area is part of the sensing electrode, wherein the first area is formed of a same material as the second area.

20. The touch panel of claim 1, wherein the opening pattern includes a first sub-pattern, a second sub-pattern and an open area is provided between the first sub-pattern and the second sub-pattern, and the first area is electrically connected to the second area by the open area.

* * * * *